United States Patent [19]

Wilson et al.

[11] Patent Number: 5,734,083
[45] Date of Patent: Mar. 31, 1998

[54] SERTRALINE POLYMORPH

[75] Inventors: Andrew Joseph Wilson; Casimir Antczak, both of Aurora, Canada

[73] Assignee: Torcan Chemical Ltd., Aurora, Canada

[21] Appl. No.: 649,401

[22] Filed: May 17, 1996

[51] Int. Cl.$^6$ .................................................. C07C 211/42
[52] U.S. Cl. .................................................. 564/308
[58] Field of Search ........................... 564/308; 514/647

[56] References Cited

U.S. PATENT DOCUMENTS 4,536,518  8/1985  Welch, Jr. et al. ...................... 514/647
5,248,699  9/1993  Sysko et al. ........................... 514/647

Primary Examiner—Richard L. Raymond
Attorney, Agent, or Firm—Robert G. Hirons

[57] ABSTRACT

A novel polymorph of sertraline hydrochloride, i.e. (1S-cis)-4-(3,4-dichlorophenyl)-1,2,3,4-tetrahydro-N-methyl-1-naphthalenamine hydrochloride, is disclosed, having improved water solubility along with acceptable stability. It is characterized by a unique x-ray diffraction pattern and unit cell structure, as well as IR and NMR spectral characteristics.

1 Claim, 3 Drawing Sheets

SERTRALINE POLYMORPH

This invention relates to the pharmaceutically active compound (1S-cis)-4-(3,4-dichlorophenyl)-1,2,3,4-tetrahydro-N-methyl-1-naphthalenamine, known and referred to herein by its generic name sertraline. More particularly, the invention relates to novel forms of sertraline, pharmaceutical compositions thereof and processes for the preparation thereof.

BACKGROUND OF THE INVENTION AND PRIOR ART

Sertraline has the following structural chemical formula:

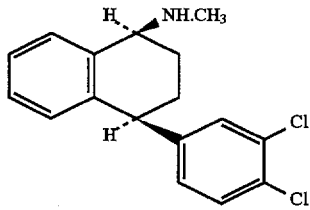

It is marketed in the form of its hydrochloride, as an antidepressant and anorectic agent.

U.S. Pat. No. 4,536,518 Welch et al., issued Aug. 20, 1985, describes the synthesis and basic activities of the family of compounds including sertraline.

U.S. Pat. No. 5,248,699 Sysko et al., issued Sep. 28, 1993, discloses novel crystalline forms of sertraline hydrochloride, and reports five allegedly novel polymorphic forms, differing from one another in respect of their physical properties, stability, spectral data and methods of preparation. They are designated Form I, Form II, Form III, Form IV and Form V. Following the procedures disclosed in U.S. Pat. No. 4,536,518 is reported to lead to the preparation of the Form II product. The Form I product, however, is reported to have the greatest stability, and to be the most suitable for formulation. It is characterized, inter alia, by exhibiting an X-ray powder diffraction pattern with characteristic peaks expressed in degrees 2θ at approximately 7.1, 12.7, 14.1, 15.3, 15.7, 21.2, 23.4 and 26.3. It is prepared, according to this patent to Sysko et al., by crystallizing sertraline hydrochloride using an organic solvent such as ethyl acetate, over a period of about 3 hours at a temperature from about 20° C. to about 100° C.

We have prepared sertraline hydrochloride Form I, in our laboratory, as well as some other sertraline hydrochloride polymorphs according to the Sysko et al. patent. The sertraline hydrochloride Form I, whilst stable as reported, is extremely insoluble. Its dissolution rate is in fact too slow to provide adequate bioavailability of the active ingredient in pharmaceutical formulations.

Accordingly, it is an object of the present invention to provide a novel form of sertraline hydrochloride, with acceptable bioavailability and other required pharmaceutical characteristics.

It is a further object of the invention to provide a process of preparing a novel, pharmaceutically acceptable form of sertraline hydrochloride.

SUMMARY OF THE INVENTION

In accordance with the present invention, there is provided a novel polymorph of sertraline hydrochloride, herein designated polymorph T1, which has acceptability stability, but which has enhanced solubility in aqueous fluids and hence much improved bioavailability as compared with Form I sertraline hydrochloride. The novel polymorph T1 exhibits characteristic analytical data which clearly differentiate it from all previously reported forms of sertraline hydrochloride. These include:

a crystalline structure with a unit cell, as determined by X-ray powder diffraction measurements, of the following approximate dimensions:
a=17.142(3) Angstroms;
b=31.154(9) Angstroms;
c=11.968(3) Angstrom
$\alpha$=90.00
$\beta$=102.63(5)
$\gamma$=90.00
V=6236.6($\alpha$) $A^{o3}$.

an X-ray powder diffraction pattern having characteristic, indicative reflections at 14.69 Å, 8.07 Å, 5.44 Å, 3.88 Å and 3.48 Å;

and an infrared absorption spectrum in potassium bromide having characteristic absorption bands expressed in reciprocal centimeters at approximately 2932.2; 2702.2; 1587.1; 1389.1; 1300,9; 1330.1; 1213.7; 1134.4; 1103.1; 1076.7; 1029.3; 957.1; 884.6; 820.7; 776.4; 739.8; 708.5; and 679.2.

The unit cell is defined by the length of the sides of the cell, parameters A, B and C above; by the relative angles of the cell sides, $\alpha$, $\beta$ and $\gamma$ above; and by the volume of the cell, V. Methods of measuring and interpreting x-ray powder diffraction measurements to obtain unit cell dimensions are well known in the art, and are recognized as characterizing the crystalline nature and structure of a product.

The present invention also relates to pharmaceutical compositions comprising an effective amount of the above described novel polymorph T1 of sertraline hydrochloride along with pharmaceutically acceptable carriers. The invention also relates to the use of such compositions of the novel sertraline hydrochloride polymorph T1 in treating conditions such as depression, anxiety-related disorders, obesity and chemical dependency in a human patient, by administering effective amounts of said composition to the patient.

The process by which the novel polymorph T1 is obtained is generally as follows. A slurry or solution of sertraline free base in an organic non-polar solvent such as toluene is treated with a polar solvent such as ethyl acetate, diethyl ether or mixtures thereof, so as to form a solution of the sertraline free base in the polar solvent. A separate batch of the organic solvent is taken and cooled, e.g. to 0°–10° C., and hydrogen chloride gas is passed into it, to prepare a solution which is about 1–10% (w/w) in hydrogen chloride. This is added to the sertraline free base solution slowly, with moderate agitation. The mixture is subjected to moderate agitation, at room temperature over a period of about 8–12 hours. A crystalline solid forms, which is separated by cooling and vacuum filtering, to give the novel polymorph T1 as a white to off-white solid, forming a fine powder on drying.

BRIEF REFERENCE TO THE DRAWINGS

DESCRIPTION OF THE PREFERRED EMBODIMENTS

Figure 1:
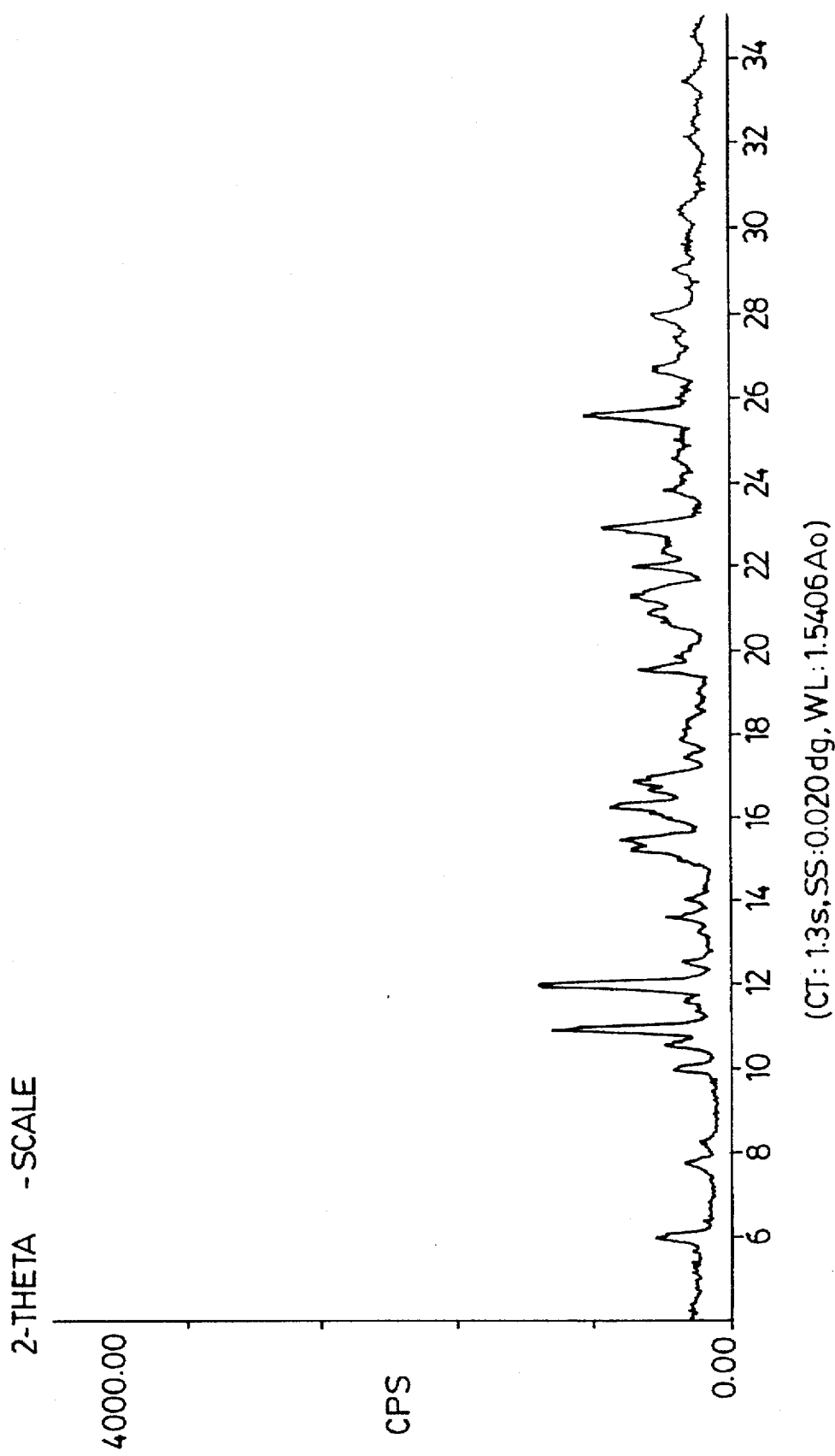
FIG. 1 is a powder X-ray diffraction pattern of the novel sertraline hydrochloride polymorph T1 according to the present invention, prepared according to Example 1 below.

The preferred process according to the present invention uses ethyl acetate as the polar solvent for the sertraline free base. The process suitably uses a sertraline salt such as sertraline mandelate as the starting material, a salt which is useful in the separation of optical isomers of sertraline. A slurry or solution of this salt in a polar organic solvent such as methanol is prepared, and an aqueous base is added to hydrolyze the salt and form the free sertraline base, under agitation. Then an organic, non-polar solvent such as toluene, followed by water, is added under agitation, to form a two phase mixture with the sertraline free base dissolved in the organic layer. The mixture is suitably filtered before separation of the two liquid phases, and the organic layer is separated. After suitable adjustment of the volume of liquid, e.g. by distillation under reduced pressure, a portion of the polar organic solvent, preferably ethyl acetate, is added and the mixed solution is cooled. A separate solution of hydrogen chloride in the polar solvent, such as ethyl acetate, is prepared and cooled, and added to the sertraline free base solution under agitation. The amount of hydrogen chloride is best adjusted to be approximately stoichiometric with respect to the sertraline free base. The novel polymorph of sertraline hydrochloride gradually forms as a crystalline solid over an extended period of time, approximately 10 hours under mild agitation, with the temperature being maintained in the approximate range 20°–25° C. The product is separated by cooling followed by vacuum filtration, to obtain a fine white-to-off white filter cake. The filter cake may be dried in vacuo at temperatures of 60°– 65° C. to obtain the final product as a fine white-to-off white powder.

The dosage rates and dosage formulations of the sertraline hydrochloride polymorph T1 of the present invention are substantially similar to those proposed and used for previously known sertraline hydrochloride forms, except that advantage can be taken of the greater solubility and bioavailability of the T1 polymorph of the present invention to prepare less concentrated dosage forms and administer smaller quantities to patients. For use in treating depression or anorexia, the dosage form may be oral or parenteral, and the daily dosage rate is normally in the range of 0.1–10 mg per kg body weight. It may be administered alone or in a formulation with pharmaceutically acceptable carrier. It can be in the form of orally administrable tablets, capsules or lozenges or the like, along with carriers and excipients such as calcium carbonate, calcium phosphate, sodium citrate, starch, PVP, sucrose, etc., in accordance with known practice.

The invention is further described and illustrated in the following specific example.

SPECIFIC DESCRIPTION OF THE MOST PREFERRED EMBODIMENTS

Example

A 1-liter 3-necked round bottomed flask, equipped with a mechanical stirrer, thermometer, and addition funnel, was purged with nitrogen. A nitrogen atmosphere was maintained throughout the reaction. To the flask was added 60.0 g of cis-(1S,4S)-N-methyl-(3,4-dichlorophenyl)-1,2,3,4-tetrahydro-1-naphthalenamine, R-(−)-mandelic acid salt (sertraline mandelate), and 180 ml of methanol. The mixture was agitated, while warming to 35°–40° C. A white slurry of volume 210 ml, was obtained.

To the above batch, while maintaining a temperature of 35°–40° C., there was added dropwise 5.7 g of sodium hydroxide dissolved in 5.7 ml water. The addition time was 1–3 minutes, to obtain a batch volume of about 225 ml, of a white slurry—colourless solution. This batch was agitated for 1 hour, at the 35°–40° C. temperature, and a colourless solution obtained.

To this solution, at the same temperature, there was added 180 ml of toluene followed by 300 ml of water, and this mixture was agitated for 15 minutes and cooled to 20°–25° C. All solids were thereby dissolved.

To the solution obtained as above, there was added 1.2 g of activated charcoal (Darco KB), 5.0 g of filtration aid (Celite), and 60 ml of toluene, and the mixture was agitated at 20°–25° C. for about 30 minutes. Then it was vacuum filtered through 15.0 g of Celite. The flask and filter cake were washed with 60 ml of toluene. The filtrate had a volume of 810 ml, and the appearance of two liquid phases.

The aqueous layer was separated, at room temperature. The organic layer was washed with water.

The toluene phase was distilled at reduced pressure using a water aspirator, until the batch volume was about 130–150 ml, i.e. about half of the initial volume. The organic solution was warmed, under moderate agitation, to about 60° C., and 600 ml of ethyl acetate was added, followed by cooling of the mixed solution to 20°–25° C.

In a separate, 250 ml 3-necked round bottom flask, equipped with a magnetic stirrer and under a nitrogen atmosphere, there was charged 120 ml of ethyl acetate, cooled to 0°–10° C., and then, maintaining the temperature below 10° C., 5.7 g of hydrogen chloride was bubbled into the solution. The resulting HCL/ethyl acetate solution is 5.0% (w/w). The total equivalents of hydrogen chloride is 1.2 equivalents with respect to the starting sertraline mandelate. This hydrogen chloride/ethyl acetate solution was maintained at a temperature below 10° C. until use in the step below.

The hydrogen chloride/ethyl acetate solution was added to the mixed toluene/ethyl acetate solution of sertraline free base, over a period of 15–30 minutes, maintaining the mixture at 20°–25° C. with moderate agitation. A slightly green, very thick gel began to form immediately upon acidification. This material then gradually formed a crystalline solid over approximately 10 hours. A temperature of 20°–25° C. was maintained with moderate agitation for the 10 hour period. The suspension was then cooled to a temperature of 0°–5° C. and agitated for a further period of 2 hours. The suspension was vacuum filtered through a Buchner funnel. The filter cake and flask were rinsed with two aliquots of 30 ml ethyl acetate, and cooled to 0.5° C. The wet filter cake was dried in vacuo at an oven temperature of 60°–65° C., for about 20 hours, to obtain a dry cake weighing 39–41 g (87–92%), with the appearance of a fine white powder.

The product was subjected to x-ray crystallographic analysis, IR analysis and NMR analysis, using standard techniques well known in the art. FIG. 1 of the accompanying drawings is the powder x-ray diffraction pattern obtained (using copper x-ray source). The horizontal axis is in degrees 2θ, these values being readily convertible to Angstrom spacings by use of standard calculations. Table 1 given below gives the x-ray powder diffraction data in Angstrom spacings. The most indicative reflections are those at 14.69, 8.07, 7.37, 5.44, 3.88 and 3.48 Å.

TABLE

| No | D-space | $I_x/I_o$ | h k l |
|---|---|---|---|
| 1. | 14.6933 | 39 | 1 1 0 |
| 2. | 11.4029 | 24 | 1 2 0 |
| 3. | 10.7475 | 16 | 1 0 −1 |
| 4. | 8.8187 | 30 | 1 3 0 |
| 5. | 8.3553 | 35 | 2 0 0 |
| 6. | 8.0699 | 93 | 2 1 0 |
| 7. | 7.6144 | 24 | 1 2 1 |
| 8. | 7.3671 | 100 | 2 2 0 |
| 9. | 7.0600 | 25 | 1 4 0 |
| 10. | 6.7683 | 16 | 1 3 1 |
| 11. | 6.5119 | 34 | 2 3 0 |
| 12. | 6.3060 | 24 | 1 4 −1 |
| 13. | 5.8281 | 53 | 1 1 −2 |
| 14. | 5.7376 | 57 | 0 1 2 |
| 15. | 5.4416 | 61 | 3 1 −1 |
| 16. | 5.3173 | 43 | 2 3 1 |
| 17. | 5.2481 | 51 | 3 2 0 |
| 18. | 5.0826 | 24 | 2 2 −2 |
| 19. | 4.5364 | 48 | 3 4 0 |
| 20. | 4.4632 | 28 | 1 6 1 |
| 21. | 4.2916 | 36 | 2 6 −1 |
| 22. | 4.2459 | 43 | 4 0 −1, 3 3 1 |
| 23. | 4.1710 | 52 | 3 3 −2 |
| 24. | 4.0390 | 50 | 4 2 0 |
| 25. | 3.8757 | 66 | 4 3 0 |
| 26. | 3.7313 | 34 | 2 6 −2 |
| 27. | 3.6208 | 29 | 1 0 3 |
| 28. | 3.4763 | 75 | 4 3 1 |
| 29. | 3.3389 | 39 | 2 6 2 |
| 30. | 3.1891 | 41 | 3 8 0, 3 7 −2 |
| 31. | 3.0726 | 28 | 5 4 0, 4 7 −1 |
| 32. | 2.9469 | 25 | 5 5 0, 3 6 −3 |
| 33. | 2.6753 | 24 | 4 1 −4, 5 7 0 |

Lattice: Monoclinic, P-type:
a = 17.142(3) A°,
b = 31.154(9) A°,
c = 11.968(3) A°,
α = 90.00
β = 102.63(5)
γ = 90.00
V = 6236.6(2) A$^{o3}$.

Figure 2:
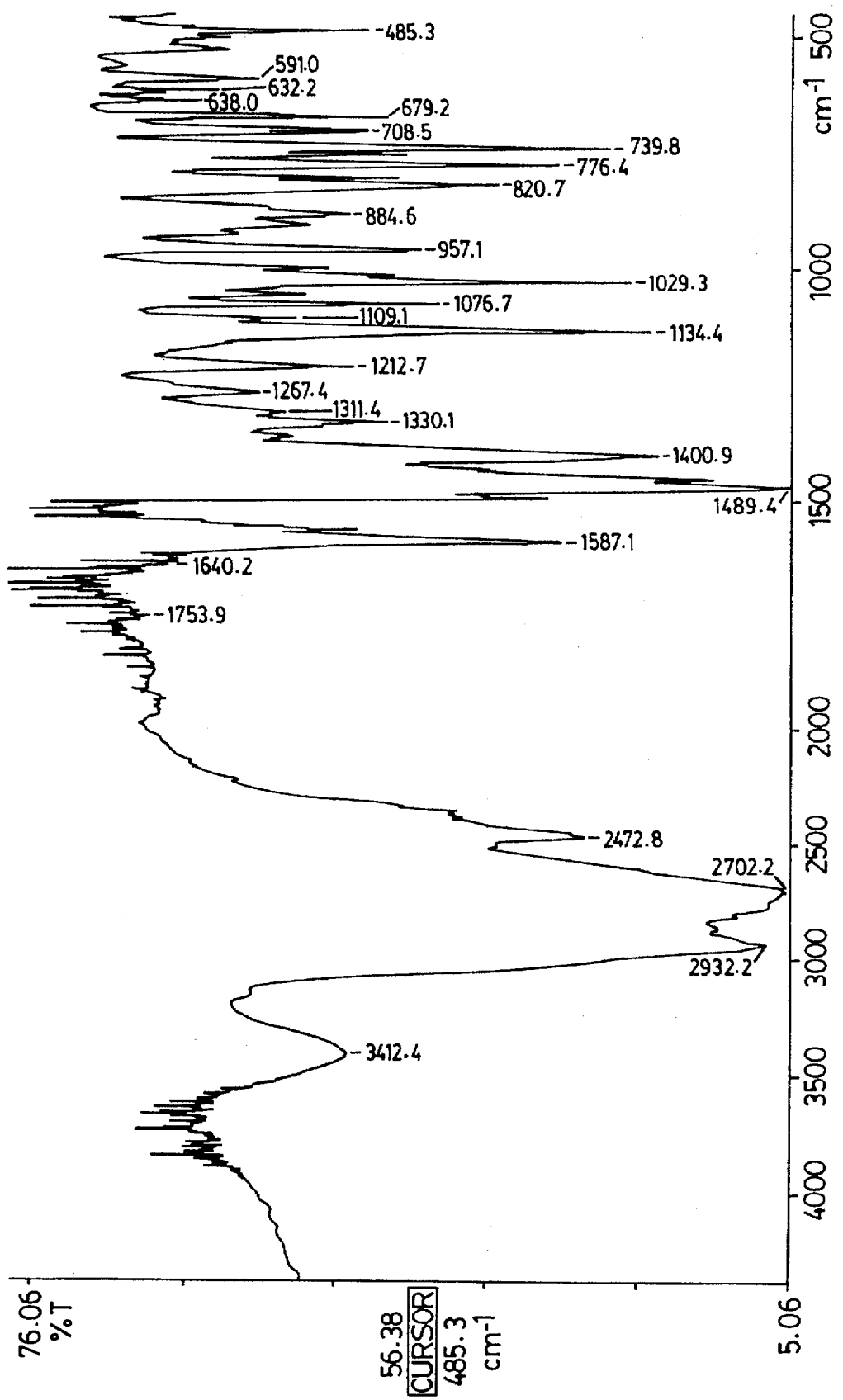
FIG. 2 is an IR spectrum of the novel sertraline hydrochloride polymorph T1 prepared according to Example 1 below.

FIG. 2 of the accompanying drawings shows the IR spectrum of the product produced according to this Example, prepared in potassium bromide pellets. It shows the following characteristic absorption bands, expressed in reciprocal centimeters: 2932.2; 2702.2; 1587.1; 1389.1; 1300,9; 1330.1; 1213.7; 1134.4; 1103.1; 1076.7; 1029.3; 957.1; 884.6; 820.7; 776.4; 739.8; 708.5; and 679.2.

Figure 3:
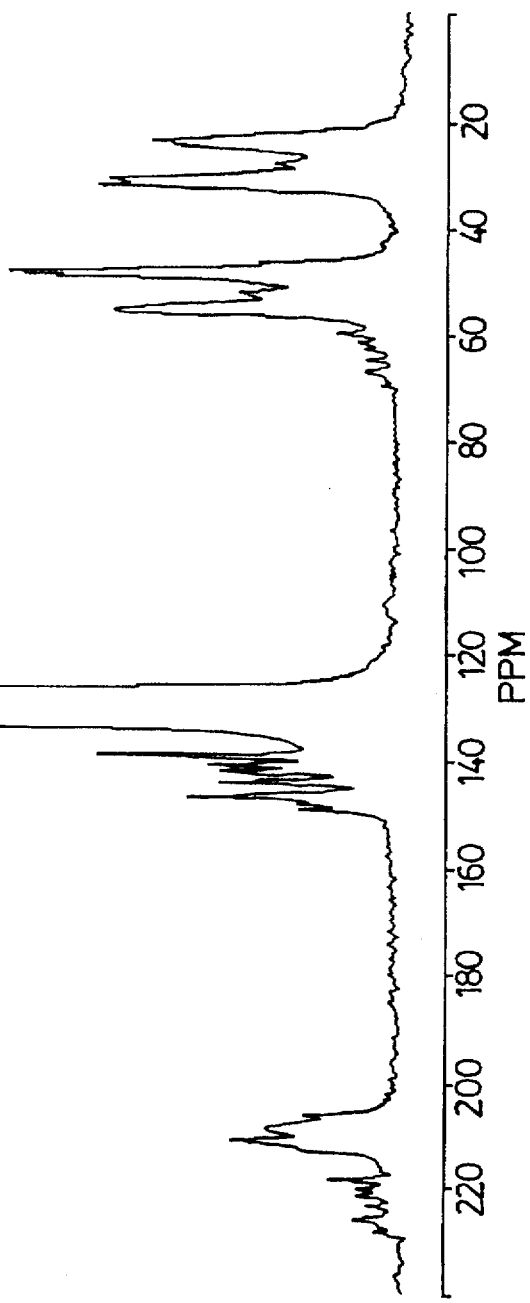
FIG. 3 is a solid state NMR spectrum of the novel sertraline hydrochloride polymorph T1 prepared according to Example 1 below.

FIG. 3 shows the NMR spectrum of the product. Solid-state $^{13}$C NMR spectra were obtained on a Bruker AX-250, 250 MHZ spectrometer, using high power proton decoupling and cross-polarization with magic-angle spinning at approximately 5 KHZ. The magic-angle was adjusted using the Br signal of KBr by detecting the side bands as described by Frye and Maciel (J. Mag. Res., 1982, 48, 125). Approximately 300 mg of sample packed into a canister-design rotor was used for the experiment. The chemical shifts were referenced to external tetrakis (trimethylsilyl) silane (methyl signal at 3.50 ppm).

The characteristic signals are as follows: ppm: 23.4, 24.3, 27.6, 30.3, 31.6, 46.5, 47.3, 48.6, and 55.3.

What is claimed is:

1. A sertraline hydrochloride polymorph characterized by:

a crystalline structure with a unit cell, as determined by x-ray powder diffraction measurements, of the following approximate dimensions:
  a=17.142(3) Angstroms;
  b=31.154(9) Angstroms;
  c=11.968(3) Angstrom
  α=90.00
  β=102.63(5)
  γ=90.00
  V=6236.6(α) A$^{o3}$;

further characterized by an x-ray powder diffraction pattern having characteristic, indicative reflection at 14.63 Å, 8.07 Å, 5.44 Å, 3.88 Å and 3.48 Å;

and further characterized by an infrared absorption spectrum in potassium bromide having characteristic absorption bands expressed in reciprocal centimeters at approximately 2932.2; 2702.2; 1587.1; 1389.1; 1300.9; 1330.1; 1213.7; 1134.4; 1103.1; 1076.7; 1029.3; 957.1; 884.6; 820.7; 776.4; 739.8; 708.5; and 679.2.

* * * * *